(12) United States Patent
Sbodio et al.

(10) Patent No.: US 11,033,216 B2
(45) Date of Patent: Jun. 15, 2021

(54) AUGMENTING QUESTIONNAIRES

(71) Applicant: International Business Machines Corporation, Armonk, NY (US)

(72) Inventors: Marco Luca Sbodio, Castaheany (IE); Spyros Kotoulas, Dublin (IE); Daniel Rejniak, Malahide (IE); James Shannon, Raheny (IE); Nagesh Yadav, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 277 days.

(21) Appl. No.: 15/782,116

(22) Filed: Oct. 12, 2017

(65) Prior Publication Data

US 2019/0110728 A1    Apr. 18, 2019

(51) Int. Cl.
*A61B 5/16* (2006.01)
*G06F 3/01* (2006.01)
(Continued)

(52) U.S. Cl.
CPC .............. *A61B 5/167* (2013.01); *A61B 5/165* (2013.01); *G06F 3/015* (2013.01); *G09B 7/00* (2013.01); *G09B 7/02* (2013.01)

(58) Field of Classification Search
CPC ......... A61B 5/167; A61B 5/165; G06F 3/015; G09B 7/00
(Continued)

(56) References Cited

U.S. PATENT DOCUMENTS 6,363,145 B1  3/2002 Shaffer et al.
8,214,214 B2  7/2012 Bennett
(Continued)

FOREIGN PATENT DOCUMENTS

CN    105306703 A    2/2016
CN    105832350 A    8/2016
(Continued)

OTHER PUBLICATIONS

Vicsi et al., "Emotional State Recognition in Customer Service Dialogues Through Telephone Line", Cognitive Information (CogInfoCom), 2011 2nd International Conference on, Jul. 7-9, 2011, IEEE Xplore Aug. 30, 2011.
(Continued)

*Primary Examiner* — Robert P Bullington
(74) *Attorney, Agent, or Firm* — Scully, Scott, Murphy & Presser, P.C.; Kurt Goudy

(57) ABSTRACT

A system, method and computer program product for augmenting, in real-time, queries/questionnaires administered to a subject by coupling the physiological response of the subject for a given question-answer pair. Further, a method/system augments/annotates answers to questionnaires/surveys/etc. with automatically detected physiological or emotional reactions of the person answering the question/survey/etc. In an embodiment, methods are implemented to: create an augmented representation of question-answer-emotion (i.e., annotating questions/answers from assessments to physiological reactions); and consider the augmented representation and the user profile to suggest actions based on such associations. In one aspect, the augmented/annotated answers are used to suggest/recommend actions to the person conducting the questionnaire/survey, where actions include: asking further questions to clarify a topic/problem, asking for clarification regarding a given answer, or asking for clarification regarding inconsistencies in answers or asking follow-up questions.

16 Claims, 7 Drawing Sheets

(51) Int. Cl.
*G09B 7/00* (2006.01)
*G09B 7/02* (2006.01)

(58) Field of Classification Search
USPC .......................................................... 434/362
See application file for complete search history.

(56) References Cited

U.S. PATENT DOCUMENTS

| 9,603,564 B2 | 3/2017 | Forbes | |
|---|---|---|---|
| 2003/0059750 A1* | 3/2003 | Bindler | G06Q 10/10 434/236 |
| 2006/0036153 A1* | 2/2006 | Laken | A61B 5/0476 600/410 |
| 2009/0150919 A1* | 6/2009 | Lee | H04N 7/17309 725/10 |
| 2010/0221687 A1* | 9/2010 | Forbes | G06K 9/00308 434/236 |

FOREIGN PATENT DOCUMENTS

| CN | 105913046 A | 8/2016 |
|---|---|---|
| DE | 10 2014 111 77 A1 | 6/2015 |

OTHER PUBLICATIONS

Schuller et al., "Recognising realistic emotions and affect in speech: State of the art and lessons learnt from the first challenge", 2011 Elsevier B.V., revised Dec. 21, 2010; accepted Jan. 20, 2011.

Li et al., "Global Clock Synchronization in Sensor Networks" INFOCOM 2004. Twenty-third Annual Joint Conference of the IEEE Computer and Communications Societies; Mar. 7-11, 2004, IEEE Xplore: Nov. 22, 2004.

Goethals, "Survey on Frequent Pattern Mining", HIIT Basic Research Unit, Department of Computer Science, University of Hesinki, Helsinki, Finland, 2003, pp. 1-43.

* cited by examiner

AUGMENTING QUESTIONNAIRES

FIELD

The invention relates to systems and methods for augmenting/annotating answers to questionnaires/surveys and the like, and more particularly, a system, method and computer program product for augmenting questions/annotating answers based on detected physiological or emotional reactions of the person answering the questionnaire/survey.

BACKGROUND

Assessments and questionnaires are key tools in the variety of disciplines.

In the health and social care domain, a client or interviewee (i.e., a human subject) is often interviewed over the phone or in person. The care worker follows a sequence of questions in a questionnaire designed to elicit certain information for this process. Based on the answers given, the care worker decides the follow up assessments or actions.

SUMMARY

According to an embodiment, a system, method and computer program product are provided for obtaining additional insight into a subject's condition by coupling a detected physiological response of the subject for a given question-answer pair.

The system and methods further provide additional/follow-up questions based on the detected physiological response of the subject captured by the system and coupled with the question-answer pair.

The system and methods may further provide additional recommendations for follow up care given the physiological response coupling.

In one aspect, there is provided a computer-implemented method to augment/annotate answers to a questionnaire. The method comprises: administering a question to a subject and receiving an answer in response; using a sensor for automatically capturing, contemporaneously with receiving he answer from the subject, a physiological or emotional reaction to the question; correlating, using a hardware processor, physiological features associated with the reaction with a time the answer is provided by the subject; generating, using the hardware processor, one or more augmented questions for the interviewer to administer to the subject based on the time-correlated physiological features and provided answer.

According to another embodiment, there is provided a computer-implemented system to augment/annotate answers to a questionnaire. The system comprises: a memory storage device, and a hardware processor, associated with he memory storage device, and configured to perform a method to: administer a question to a subject and receiving an answer in response; use a sensor for automatically capturing, contemporaneously with receiving the answer from the subject, a physiological or emotional reaction to the question correlate physiological features associated with the reaction with a time the answer is provided by the subject; generate one or more augmented questions for an interviewer to administer to the subject based on the time-correlated physiological features and provided answer.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE DRAWINGS

Similar or functionally similar elements in the figures have been allocated the same reference signs if not otherwise indicated.

DETAILED DESCRIPTION OF THE EMBODIMENTS

Assessments and questionnaires, surveys, opinion polls, whether administered in a digital form, a written or oral form, are key tools in the variety of disciplines. When human subjects are involved, these tools may elicit answers in addition to physiological or emotional responses. By capturing this response information, together with the answers to the questions, the amount of information covered is increased and more granular changes in the responses of the subjects may be detected.

This is particularly important for self-assessment, where the conductor of the questionnaire is not physically present (or is the subject of the questionnaire themselves).

In the health care domain, a client (e.g., a human subject, a patient, an interviewee), is often interviewed over the phone or in person. The care worker follows a sequence of questions, e.g., in one or more questionnaires, for this interview process.

Based on the answers given, the care worker may decides the follow up questions, assessments and/or actions.

With the embodiments of the system described herein, the care worker may use captured physiological and emotional response information to gain additional insight into a client's condition by coupling the physiological response of a client for a given question-answer pair.

Figure 1:
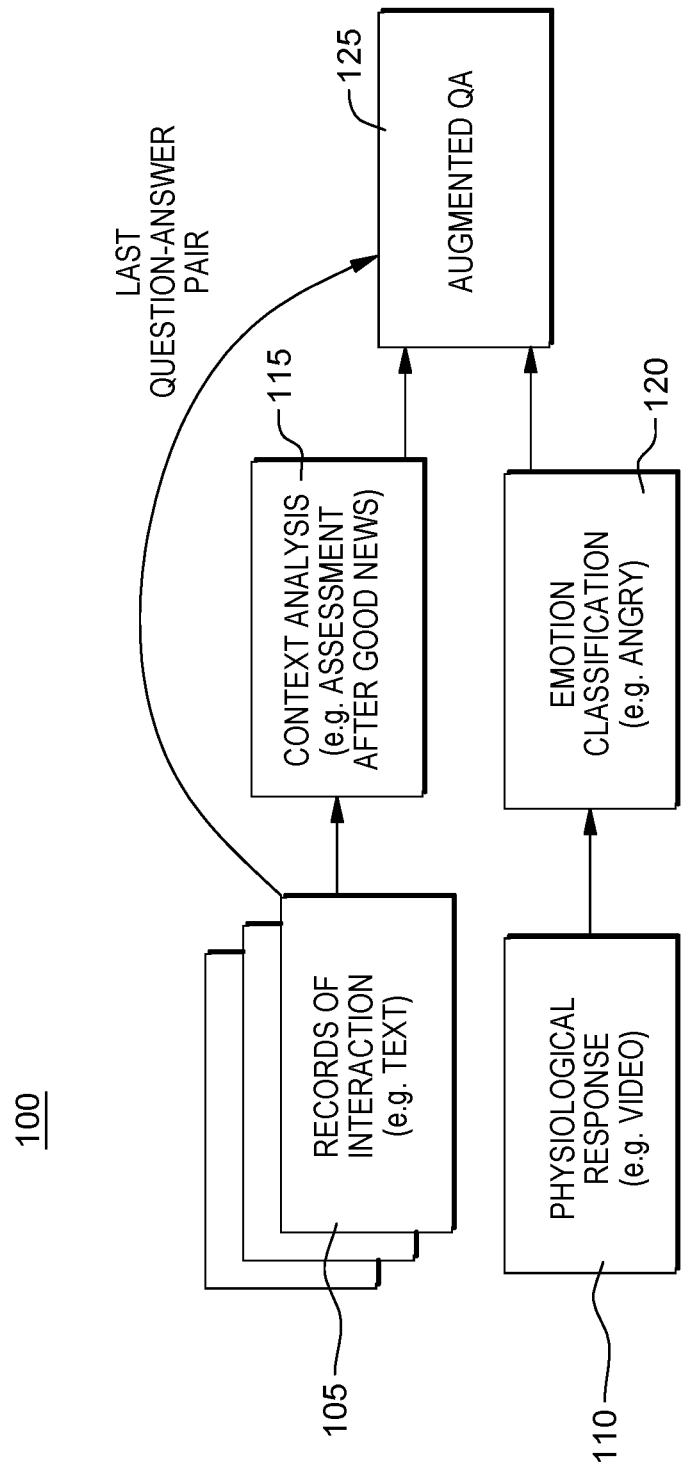
FIG. 1 depicts a conceptual implementation of a system for augmenting questionnaires in one aspect of the invention.

FIG. 1 briefly shows a conceptual implementation of a system 100 for augmenting questionnaires. Stored in a database associated with a computing system are a plurality of records 105. In one embodiment, each record includes information such as a textual description of interactions 105 between a client and interviewer. Included in these interactions may be a list of one or more questions that have been or about to be administered to the client at a particular time.

During the administering of the one or more questions from the questionnaire, sensors are invoked to capture and store the subject's physiological response and generate corresponding physiological response data with a timestamp indicating the particular time the question was administered/answered to/from the human subject. For example, as shown at 110, while the subject is giving a response to a particular question associated with assessing a client, the client's response and answer to a particular question(s) are captured by a sensor. In one embodiment, such a sensor may be a video capture device (e.g., a digital video-camera) that that captures as a video, the subject's response and answer to a particular question(s). From the captured response, the system is provided with a classifier device 120, that receives as input the subject's response (answer) to the particular question and the sensed video of the user response generated. The classifier device is configured to recognize the subject's emotion corresponding to the subject's physiological response captured in the video. In one embodiment, the recognizing of emotions may be based on observed facial and voice (speech) clues.

As a non-limiting example, a question posed by an interviewer may be "How are you feeling?" or "Are you feeling good today?" and the subject may respond accordingly, e.g., the subject may answer "Yes" that he/she is feeling good. A physiological response may be further obtained which may be classified into an emotion, e.g., happy, sad, angry, etc. As an example, the physiological response may be such that an emotion is detected that contradicts the client's answer. For example, while the client may answer that he/she is feeling "good," the classified emotion based on the physiological response, may indicate that the client is angry or sad. This may indicate to the interviewer a discrepancy as the client indicates feeling "good" while the detected emotion indicates sadness.

In one embodiment, the type of detected emotion output of the emotion classifier may be immediately communicated to the interviewer, i.e., after the administering of the question and receiving of the response. In another embodiment, the detected emotion output of the classifier may be stored in a record of interaction for subsequent communication and/or use by the interviewer at a later time.

In either scenario, the interviewer gains additional insight or clue into exactly how the client is feeling that can be used by the interviewer to generate or augment the interviewer's questioning or conduct a further action. For example, based on a detected discrepancy between the client's answer and the corresponding detected emotion, in this scenario, the interviewer may be prompted to repeat the question to the client with further detail, or even pose the question again to the inventor in a different manner.

A record of interaction 105 may thus memorialize the questions and features of the questions (keywords or concepts of questions(s)) administered (or to be administered) by the interviewer), and if applicable, optional answers returned by the client or answer features (e.g., keyword responses) returned by the client, or offered to the client to choose from. In one embodiment, the stored record is augmented with information, e.g., text, relating to the context of how the client was/is feeling, e.g., based on a recent context of the user or classified emotion. For example, if the client receives bad news two minutes ago, this may have an effect on how the client answers the next question. Thus, the next question may be augmented based on the client's current context, e.g., the current mood of the client, and or alternatively, based on the emotion classified.

At 115, received from an interaction record, an analysis module running in the system conducts an analysis of the context associated with the subject as described in the interaction record. For example, it may be the case that upon review of the context surrounding the interaction as memorialized in a record 105, there may be determined a positive or good assessment of the subject's condition based on the subject's context at the time and the question asked (e.g., an assessment of the subject's interaction is taken after receipt of "good" news). Alternatively, there may be determined a negative or bad assessment of the subject's condition based on the subject's context at the time, e.g., the subject just received "bad" news.

Additionally, at 120, the obtained physiological response as sensed by a sensing equipment, e.g., digital video recorder, speech or vocal pattern sensor/monitor, or on-body sensor(s) and captured while the subject responds to a particular question, is input to a classifier module running in the system and configured to classify an emotion of the human subject based on the physiological response when answering the question. For example, the question may elicit a physiological response from the human subject that corresponds to an emotion indicating the subject is angry, or sad or happy.

Based on the context assessment and the classification of the human subject's physiological response, and the context determined from the interaction record, the system generates an augmented QA pair 125. That is, the current question/answer pair 130 will be augmented with the physiological assessment of the user's interaction such as by coupling the physiological (emotional) response of a client for a given question-answer pair and the client's context.

As a further example, for each question administered to the client during the course of an interview/assessment, the system records a normalized score of an emotion derived from the physiological responses. For example, for an administered question (question Q1) such as "Is your relationship with your neighbors good?," a subject's elicited response (answer A1) may be "Very good". Using the classifier, a degree of emotion, in the form of an emotion score (E1), may be assessed for that subject based on a physiological response captured for that user while providing the answer. A context (C1) associated with the user at the time the question is administered may be further recorded.

In one embodiment, an emotion "score" may be generated that is a numeric value or a probability, e.g., that there is detected a certain emotion in the client's response. Example emotions may include, but are not limited to the following: "delight", "surprise", "anger", "frustration", and "sorrow". Example emotion "scores" that may be assessed for association with the transaction record may be, for example: Delight (0.2), Surprise (0.2), Anger (0.6), Frustration (0.5), and Sorrow (0.3).

Thus, in one embodiment, an augmented representation of the Q-A pair 125 may be a tuple as follows:
Augmented representation: <Q1, A1, E1> or <Q1, A1, E1, C1>

Armed with the additional knowledge, a care worker has additional insight using the clues in the response, and may be suggested to ask more related questions as a follow up.

The detecting and/or capturing of a subject's physiological response may be performed in a variety of ways. For example, automatic monitoring techniques as known in the art may be implemented to detect a degree of "discontentment" of a customer during a spontaneous conversation between a customer and a dispatcher, e.g., through a telephone discussion. That is, state of the art systems may be implemented to monitor voice patterns, e.g., to provide automatic recognition of an emotion and/or physiological reaction from the user's voice and/or speech. The system depicted in FIG. 1, provides an additional step 125 of associating the information relating to that customer's detected physiological reactions to the unstructured data such as specific questions/answers.

In a further embodiment, the system suggests actions based on such associations. For example, the system may further provide recommendations for follow up care given the physiological response coupling. For example, such actions may include, but are not limited to: asking further questions to clarify a topic/problem; asking for clarification regarding a given answer; asking for clarification regarding inconsistencies in answer; and/or asking follow-up questions.

Figure 2:
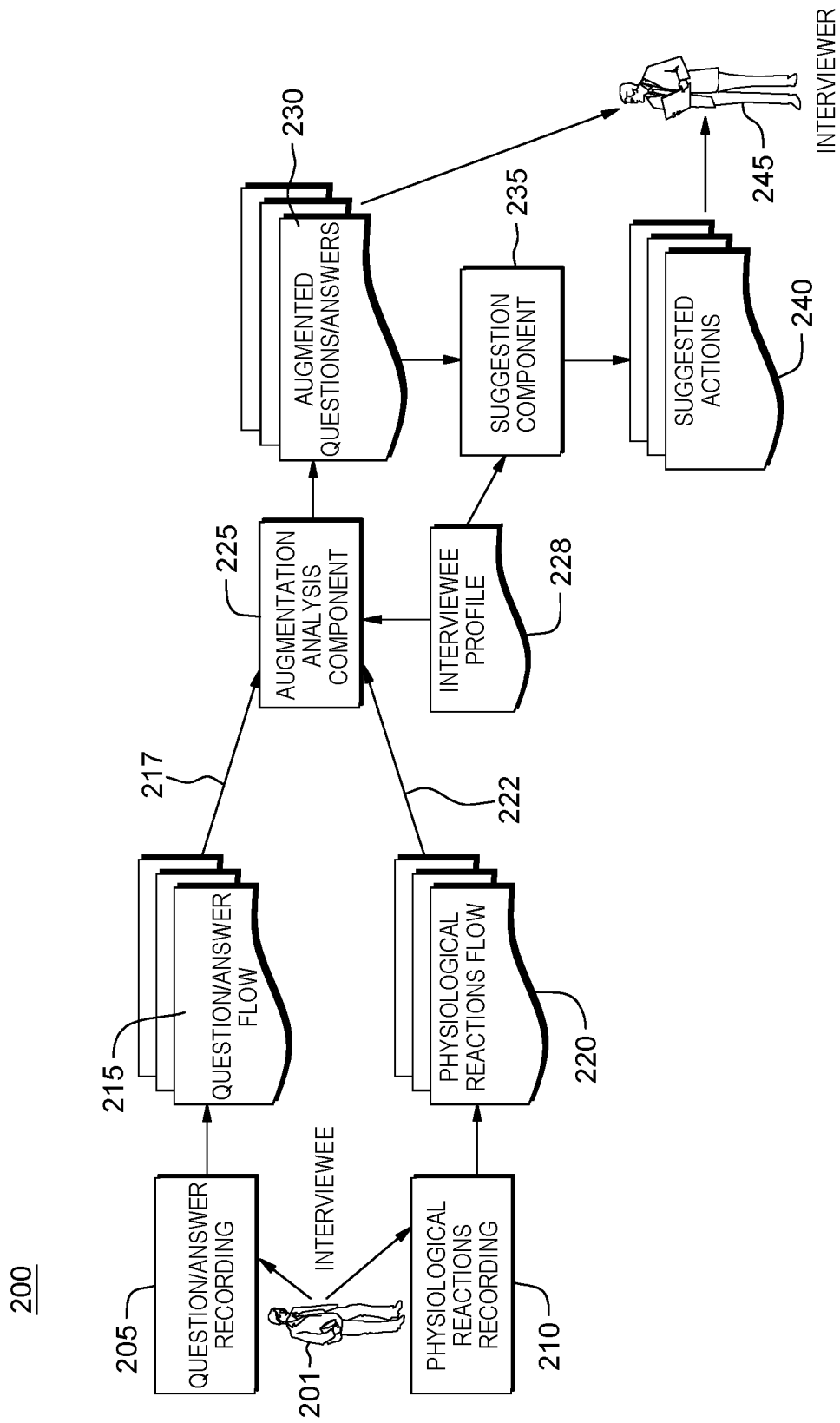
FIG. 2 depicts a first embodiment of the system used for augmenting questionnaires according to a first embodiment.

FIG. 2 shows a further diagram of a system 200 implementing the methods described with respect to FIG. 1. As shown, a human subject 201 is depicted as providing answers to questions while being simultaneously monitored to detect physiological reactions at particular (recorded) time instants. At 205, FIG. 2, the system, e.g., an interviewer, records questions and the answer content (information). At 210, a monitoring device records the subject's physiological reactions while giving answers to the questions.

At 215, the questions/answer pairs information 217 is processed and provided as a flow for input to an augmentation analysis component 225. Similarly, the subject's physiological reactions information 222 is processed and provided as a flow for input to an augmentation analysis component 225.

The augmentation analysis component 225 receives both the question/answer pair flow 217 and the physiological reactions flow 222 and performs a temporal correlation of the questions/answers flow with the real time physiological reactions flow. In one embodiment, a computing system device performs the temporal correlation between signals and user interface (UI) actions (e.g. video and user clickstream events). Then, the method implemented at component 225 correlates the physiological reactions and/or answers from the human subject with information about that subject's profile. For example, further received at the computer system is an interviewee profile 228 that includes, but is not limited to information that may further characterize the interviewee and/or his current context such as: a current medical condition (e.g., hypertension), a current physical characteristic or mental condition, (e.g., obese, suffers depression), a marital status (e.g., divorced), etc. Based on the question/answer pair flow 217, the physiological reactions flow 222 and characteristic features 228 obtained from the interviewee profile, the augmentation analysis component 225 generates additional (augmented) questions 230 to select for presentation to the interviewee. Given the additional interviewee characteristic features information 228 and the (augmented) questions, a suggestion component 240 generates suggested actions for the interviewer 245 to further present to the interviewee in conjunction with a given answer to a question presented. Such a recommended action may include, for example, asking for a clarification regarding a given answer, asking for clarification regarding inconsistencies in answers, or asking follow-up questions. As an example of detecting an inconsistency, if a question is presented to the client: "How happy do you feel with your progress towards the weight loss goal?" and the answer received from the subject is "Very happy", however the detected emotion indicates "Depression", then this combination will prompt the interviewer of a possible inconsistency with respect to the current Q/A pair.

Figure 3:
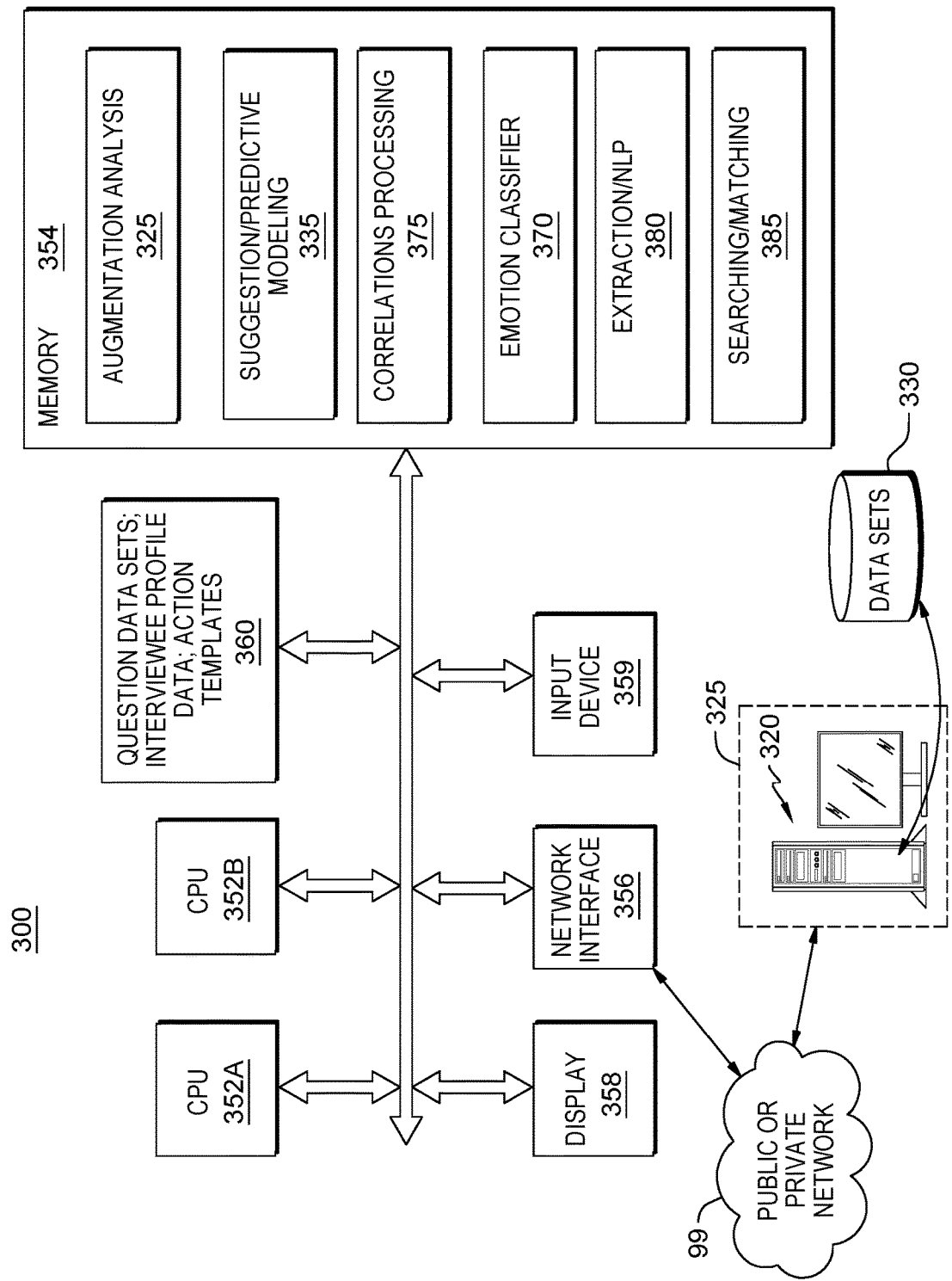
FIG. 3 depicts a system in which the present invention is employed according to an embodiment.

FIG. 3 depicts a detailed embodiment of a computer system 300 for augmenting questionnaires. In some aspects, system 300 may include a computing device, a mobile device, or a server. In some aspects, computing device 300 may include, for example, personal computers, laptops, tablets, smart devices, smart phones, or any other similar computing device.

Computing system 300 includes one or more processors 352A, 352B, a memory 354, e.g., for storing an operating system and program instructions, a network interface 356, a display device 358, an input device 359, and any other features common to a computing device. In some aspects, computing system 300 may, for example, be any computing device that is configurable to communicate with a web-site 325, web- or cloud-based server 320, or with other computing devices over a public or private communications network 99. Further, as shown as part of system 300, questions and questionnaire sets, related physiological reactions, interviewee feature profile data and recommender actions or actions templates may stored locally in an attached memory storage device 360, or otherwise may be stored in a remote memory storage device 330, e.g., a database, and accessed via a remote network connection for input to the system 300.

In the embodiment depicted in FIG. 2, processor 352A, 352B may include, for example, a microcontroller, Field Programmable Gate Array (FPGA), or any other processor that is configured to perform various operations. Processors 352A, 352B may be configured to execute instructions as described below. These instructions may be stored, for example, as programmed modules in memory storage device 354.

Memory 354 may include, for example, non-transitory computer readable media in the form of volatile memory, such as random access memory (RAM) and/or cache memory or others. Memory 354 may include, for example, other removable/non-removable, volatile/non-volatile storage media. By way of non-limiting examples only, memory 354 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 356 is configured to transmit and receive data or information to and from a web-site server 320, e.g., via wired or wireless connections. For example, network interface 356 may utilize wireless technologies and communication protocols such as Bluetooth®, WIFI (e.g., 802.11a/b/g/n), cellular networks (e.g., CDMA, GSM, M2M, and 3G/4G/4G LTE), near-field communications systems, satellite communications, via a local area network (LAN), via a wide area network (WAN), or any other form of communication that allows computing device 300 to transmit information to or receive information from the server 320.

Display 358 may include, for example, a computer monitor, television, smart television, a display screen integrated into a personal computing device such as, for example, laptops, smart phones, smart watches, virtual reality headsets, smart wearable devices, or any other mechanism for displaying information to a user. In some aspects, display 358 may include a liquid crystal display (LCD), an e-paper/e-ink display, an organic LED (OLED) display, or other similar display technologies. In some aspects, display 358 may be touch-sensitive and may also function as an input device.

Input device 359 may include, for example, a keyboard, a mouse, a touch-sensitive display, a keypad, a microphone, or other similar input devices or any other input devices that may be used alone or together to provide a user with the capability to interact with the computing device 300.

In one embodiment, programmed processing modules stored in a device memory 354 provide the system with abilities for augmenting questionnaires based on information including an interviewee's question/answer data flow and a corresponding physiological reactions data flow.

As shown in FIG. 3, one program module stored in a device memory 354 may include the augmentation analysis module 325 processing data (e.g., tuples) from the question/answer pair flow, the physiological reactions flow and invokes operations for temporally correlating the questions/answers flow with the real time physiological reactions flow. A suggestion module 335 is provided to invoke operations for generating a predictive model for predicting a recommendation for the interviewer based on accumulated data. In one embodiment, a model learning component may be implemented by a recommender system (not shown), e.g., a frequent pattern mining recommendation system. Such a recommender system is invoked to: identify common/frequent associations among information from the interviewee profile, the augmented questions/answers, and configurable templates of actions. For example, after analyzing all the records existing in the database, frequent patterns may be extracted and the extracted set of patterns is one example of the model. While making a recommendation for an interviewee, the degree of overlap between known facts about the interviewee and existing patterns is used to make recommendations. As an example template of action, the learned model may be configured to detect that majority of clients who have answered a question A with an emotion B, have been recommended an activity C. Thus a current client will also be recommended the activity C given a scenario providing question A with emotion B.

As further shown in FIG. 3, in one embodiment, a classifier module 370 is provided that invokes operations for classifying the emotion based on the detected physiological response to an interviewer's question; a correlation module 375 is provided for invoking operations for performing the temporal correlations. In an example implementation, processes may be invoked to capture the temporal correlation using a same system clock (not shown) for the physiological sensors or via synchronization of system clocks belonging to different modules of the system. One embodiment for performing temporal correlations is described in a reference to Qun Li et at. entitled "Global Clock Synchronization in Sensor Networks" (I.E.E.E. Infocom 2004) incorporated herein by reference. An extraction engine 380 may be further provided to extract characterizing features from the information contained in interviewee profile. Such an extraction engine may comprise a Natural Language Processing (NLP) engine. In one embodiment, features extraction from the interviewee profile may comprise passing the unstructured data belonging to an interviewee through an annotator to identify concepts of interest in the data. An example annotator that may be implemented may include IBM® Content Analytics with Enterprise Search, Version 3.0.0 that provides a number of Unstructured Information Management Architecture (UIMA) annotators for advanced text analysis. A searching/mapping module 385 may be further provided that performs functions for matching the temporally correlated interviewee's answers and physiological reaction data with the interviewee's profile information using textual and semantic matching to keywords. In one embodiment, semantic matching may be performed mathematically by calculating the degree of overlap between two feature vectors (e.g., a cosine similarity).

Figure 4:
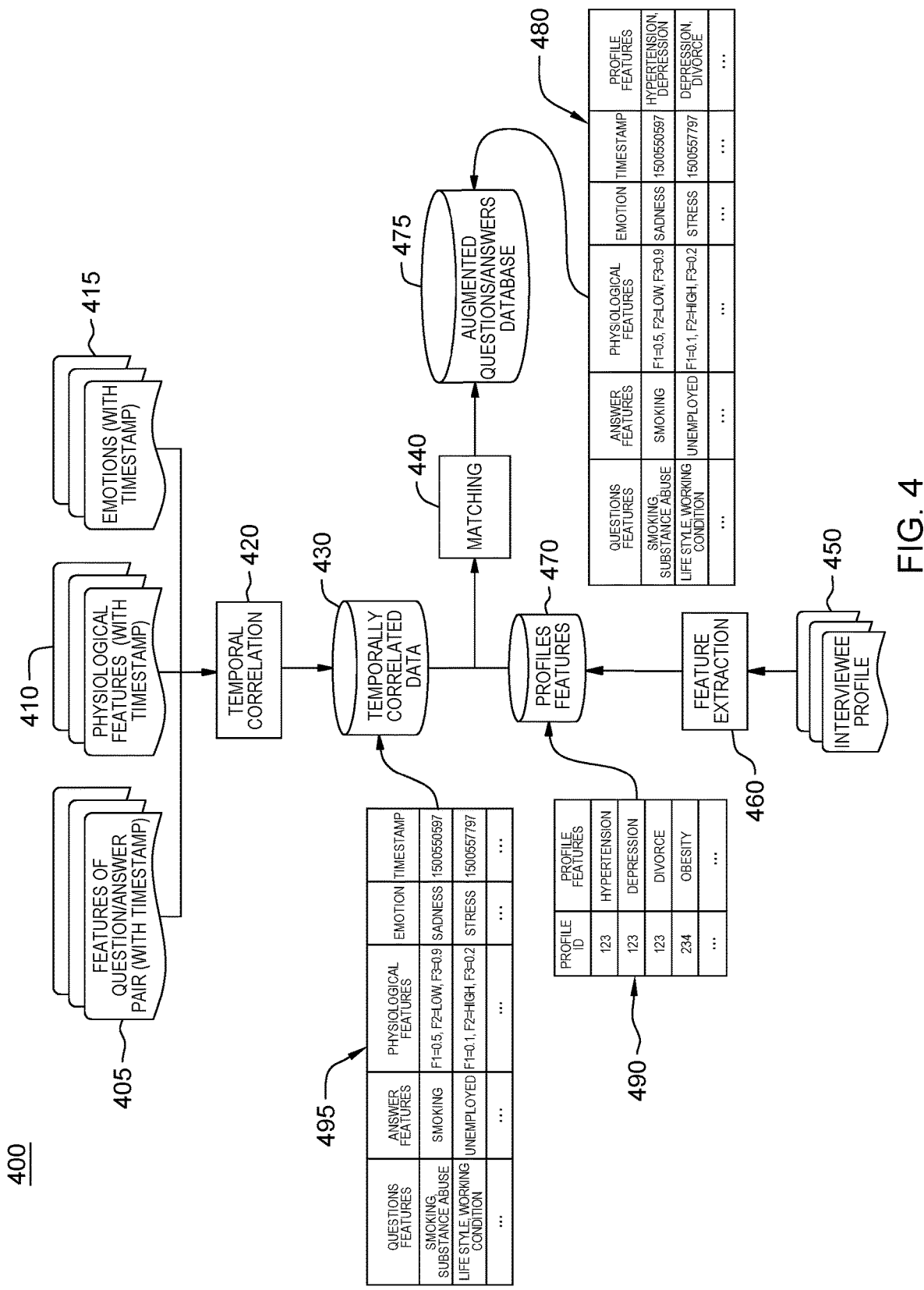
FIG. 4 depicts a more detailed embodiment of the system of FIG. 3 for augmenting questionnaires in a the health or social care domain.

FIG. 4 depicts computer-implemented operations of a further system 400 for implementing functionality to augment questionnaires using the system of 300 of FIG. 3. In the system 400, a first component administers the questions to and receives the answers from the subject (interviewee). Functional blocks are invoked to extract certain question/answer pair features 405 with associated timestamps of when the Q/A were obtained from subject. Further functional blocks are invoked to extract one or more physiological features 410 from the subject with associated timestamps of when the physiological features are obtained/measured. Further functional blocks are invoked to extract one or more emotions 415 the subject is exhibiting with associated timestamps of when the subject's emotions are observed/measured. Augmentation analysis module implements functional blocks 420 for performing temporal correlations of each of the physiological reactions, answers, and interviewee profile data, and associates such entities in a data record 495 such as may be stored in database 430. Such a database record may include question features, corresponding answer features, time correlated physiological reaction(s), time correlated emotion of the subject, and the associated timestamp.

In conjunction with this processing generating record 495, an off-line process may be implemented to obtain the subject's characteristic features. In FIG. 4, functional blocks of a feature extraction module 460 are invoked to extract certain features from the interviewee (subject) profile data 450 obtained. In one embodiment, profile features may be keyword extracted from textual information in the interviewee profile.

In one embodiment, techniques employing semantic matching or other possible entity similarity metrics, e.g., a computed semantic distance according to some vocabulary/ontology, or any string similarity metric and entity (e.g., a keyword) similarity metrics, may be used to extract a subject's profile features data.

The functional modules of feature extraction module 460 generates a data record 490 associating the profile data (e.g., depressed, divorced, obese, and hypertension) with profile ID codes that can be stored in database 470 for use by the system 300.

The system then generates further data records 480 that associates the subject's augmented question features, answer features, time correlated physiological reaction(s), time correlated emotion of the subject, and the associated timestamp with the profile data for that subject. In particular, these records may form an augmented questions/answers database 475 for use by system 300. In one embodiment, a matching module 440 is invoked for performing textual and semantic matching of keywords from the questions/answers, emotions and extracted profile features. Other techniques alternately employed may include semantic matching or other possible entity similarity metrics, e.g., computing a semantic distance, may be employed.

Figure 6:
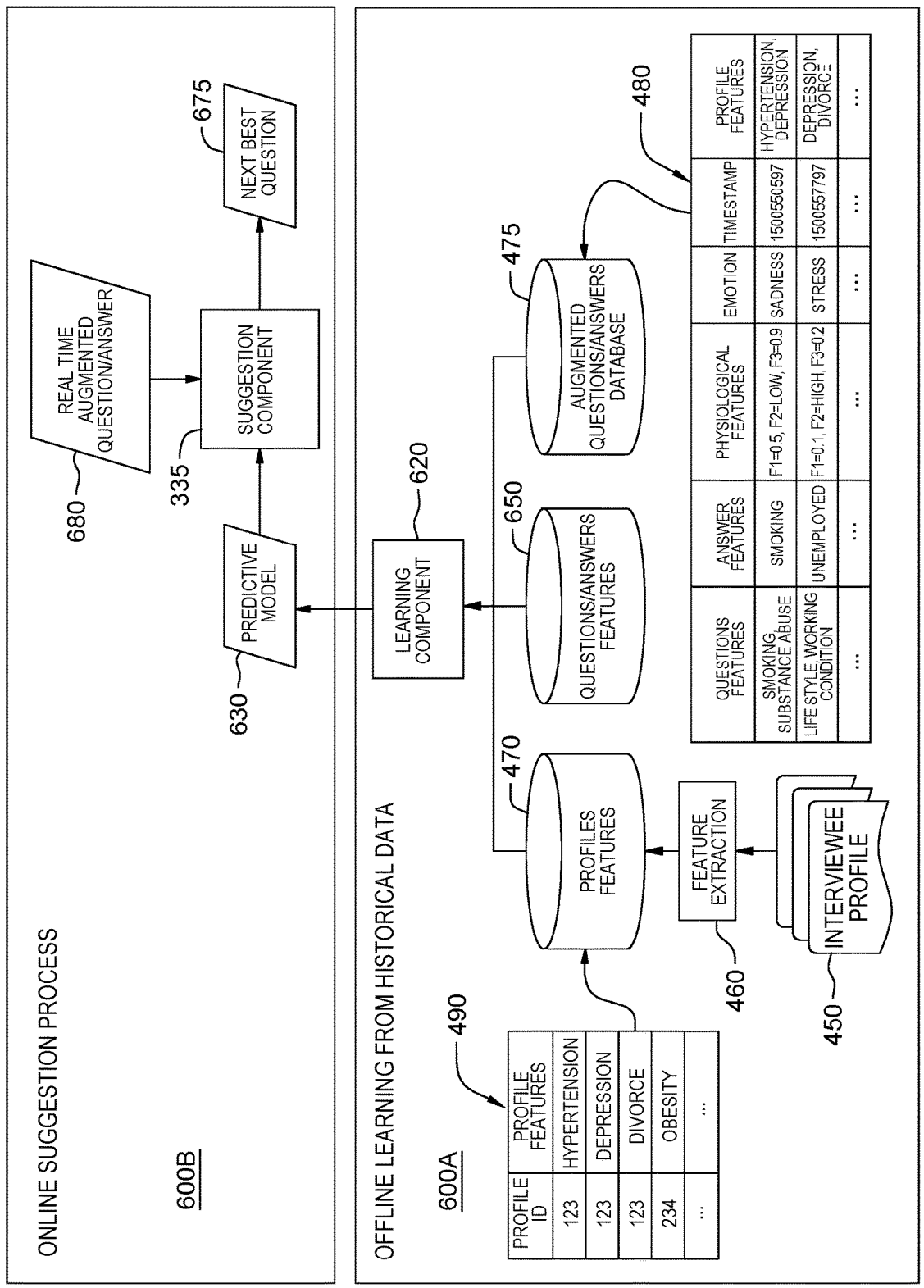
FIG. 6 shows a diagram illustrating on-line suggesting and off-line learning processes implemented in the system for augmenting questionnaires of FIG. 3.

FIG. 6 depicts the processing performed at computer system 300 which may include an "off-line" learning process 600A from historical data, and the online suggestion process 600B used to perform real-time interviews with question augmentation. In the offline learning process 600A, data from the profiles features database 470, augmented questions/answers database 475, and a set of question/answer features such as may be stored in further database 650, are collected for a plurality of subjects over time, and the historical data from these databases may be used as predictive model training data sets during the learning process. Thus, in a further embodiment, a model learning component 620 is invoked to train a predictive model at 630, e.g., in a recommender system employing, for example, frequent pattern mining, that can be used to make a recommendation for an interviewer (for the current case that the interviewer is working on).

In the real-time (on-line) interview process 600B, the predictive model 630 may then be invoked by the suggestion component 335 to recommend a next best question 675 or a real-time augmented question/answer 680. In one embodiment, a next "best" question may be the question ID that is recommended by the frequent pattern mining algorithm implemented. As mentioned, the suggestion component 335 invokes operations for extracting patterns using a frequent pattern mining recommendation system, for example, and recommends an augmented question or action to take, based on the training of a predictive model and any pattern that correlates the physiological reactions and/or answers from the human subject with characterizing features information about that subject from that subject's interviewee profile. One frequent pattern mining system that may be implemented is described in a reference to Bart Goethals entitled "Survey on Frequent Pattern Mining" HIIT Basic Research Unit, Department of Computer Science, University of Helsinki, Finland (February 2003) incorporated herein by reference.

Figure 5:
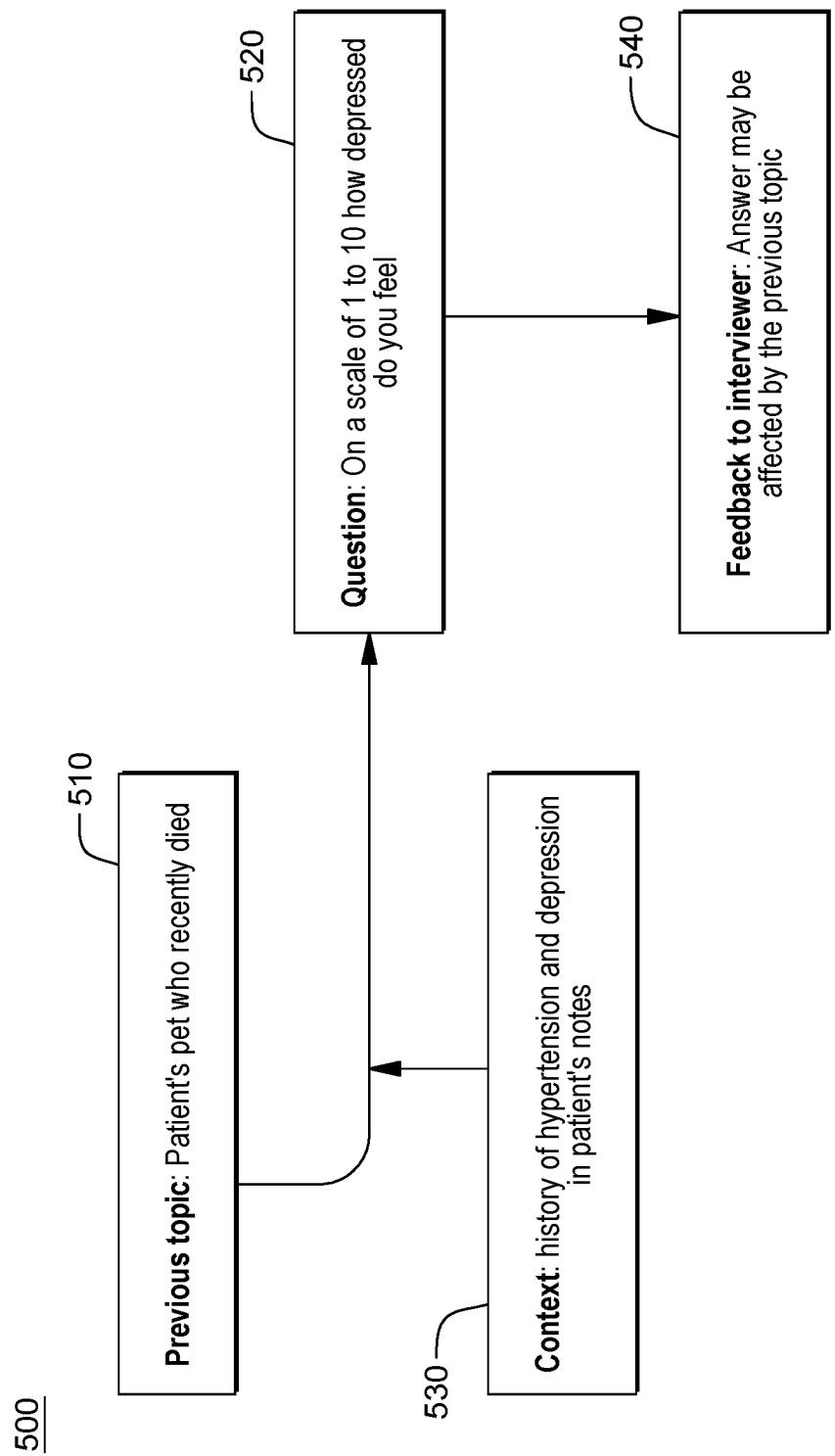
FIG. 5 depicts an example interview scenario during the conducting of the real-time (on-line) interview process of FIG. 6 in the health or social care domain.

FIG. 5 depicts an example scenario 500 during the conducting of the real-time (on-line) interview process 600B of FIG. 6. At the first step 510, it is noted that a prior topic of questioning was directed to the interviewee's pet who had recently died. It is further noted at 530 from that interviewee's extracted features profile that the interviewee has a history of depression and hypertension. Thus, given this prior topic and the determined profile context, the interviewer may augment the questioning at 520, e.g., from an action template, with a further question inquiring as to an amount of depression that the interviewee currently feels. Given the context, the system recommender may generate feedback directed back to the interviewer at 540 indicating that this answer may be affected by the previous topic of question posed. In a non-limiting embodiment, feedback presented to the interviewer may be in the form of a pop-up displayed on an output device, or as an audio clue communicated to the interviewer.

Figure 7:
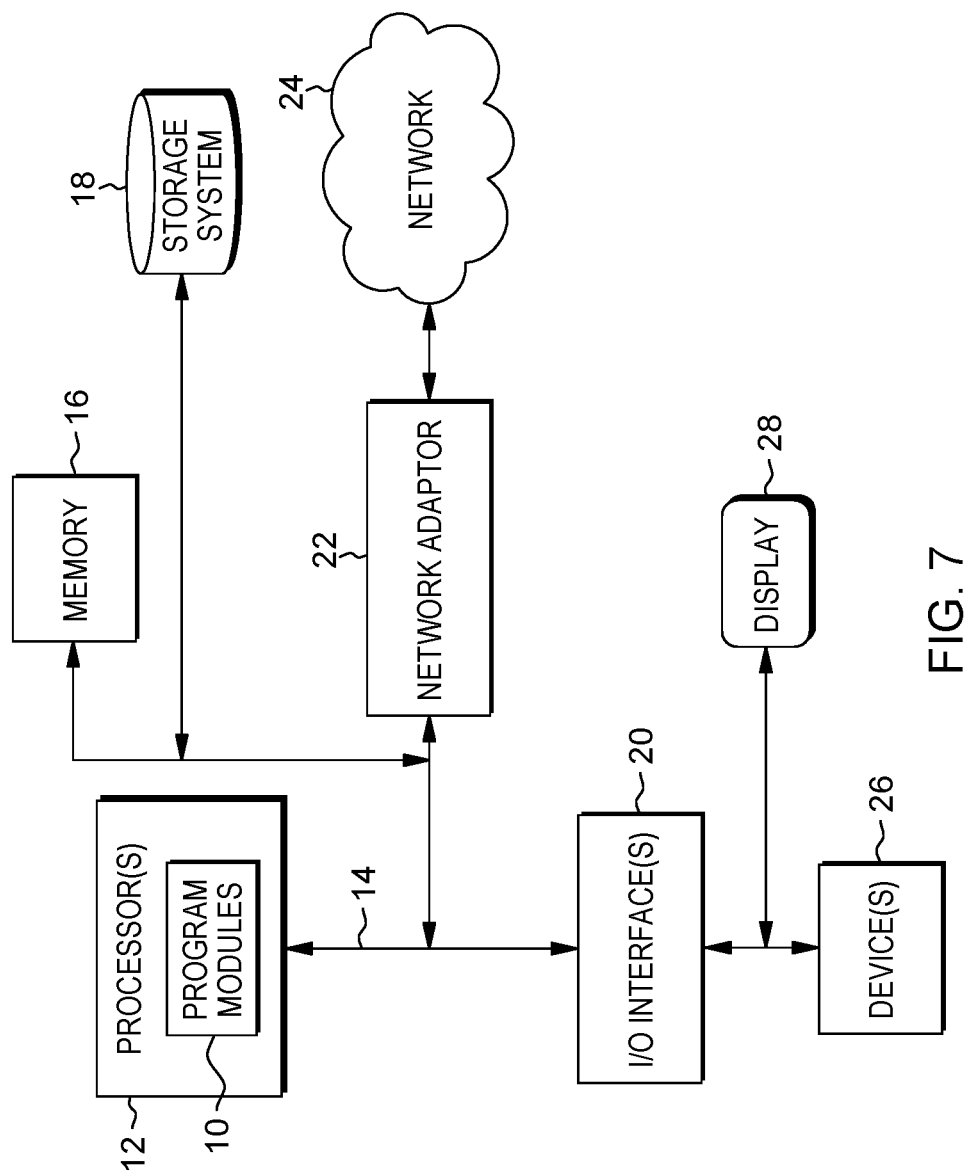
FIG. 7 illustrates an example computing system in accordance with an embodiment.

FIG. 7 illustrates an example computing system in accordance with the present invention that may provide the services and functions associated with augmenting questionnaires. It is to be understood that the computer system depicted is only one example of a suitable processing system and is not intended to suggest any limitation as to the scope of use or functionality of embodiments of the present invention. For example, the system shown may be operational with numerous other general-purpose or special-purpose computing system environments or configurations. Examples of well-known computing systems, environments, and/or configurations that may be suitable for use with the system shown in FIG. 7 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In some embodiments, the computer system may be described in the general context of computer system executable instructions, embodied as program modules stored in memory 16, being executed by the computer system. Generally, program modules may include routines, programs, objects, components, logic, data structures, and so on that perform particular tasks and/or implement particular input data and/or data types in accordance with the methods described in FIGS. 1, 2, 4 and 6.

The components of the computer system may include, but are not limited to, one or more processors or processing units 12, a memory 16, and a bus 14 that operably couples various system components, including memory 16 to processor 12. In some embodiments, the processor 12 may execute one or more modules 10 that are loaded from memory 16, where the program module(s) embody software (program instructions) that cause the processor to perform one or more method embodiments of the present invention. In some embodiments, module 10 may be programmed into the integrated circuits of the processor 12, loaded from memory 16, storage device 18, network 24 and/or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

Memory 16 (sometimes referred to as system memory) can include computer readable media in the form of volatile memory, such as random access memory (RAM), cache memory an/or other forms. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with the computer system; and/or any devices (e.g., network card, modem, etc.) that enable the computer system to communicate with one or more other computing devices. Such communication can occur via Input/Output (I/O) interfaces 20.

Still yet, the computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A computer-implemented method to augment or annotate answers to a questionnaire, the method comprising:
   receiving from a subject, via a computing system, an answer in response to a question administered to the subject by a remotely located interviewer over a communications network connection;
   using a sensor device for automatically capturing, contemporaneously with receiving said answer from the subject, a physiological reaction to the question, the sensor device integrated within a sensor network in communication with said computing system;
   temporally correlating, using a hardware processor associated with the computer system, physiological features associated with the physiological reaction with a time the answer is provided by the subject, said temporally correlating comprising invoking an operation to synchronize, using a system clock of the sensor network, said captured physiological reaction with an action event received;
   determining, at the hardware processor, an emotional state of the subject based on the correlated physiological features;
   forming, at the hardware processor, question-answer data pairs from the received answers and administered questions;
   coupling, using the hardware processor, a data representing the subject's current emotional state to current question-answer data pairs to form respective augmented question-answer tuples;
   obtaining, using said hardware processor, question features and answer features from said formed augmented question answer tuples;
   extracting, using the hardware processor, one or more profile characteristic features of the subject from a profile information corresponding to the subject, said characteristic features determined by using a natural language parsing system to perform a textual and semantic matching with keywords associated with said question features and answer features;
   forming, using the hardware processor, a database that collects, over time, historical data pertaining to a plurality of other subjects, said historical data comprising data records associating, for each respective other subject: past administered question features and corresponding received answer features associated with a question administered to the respective other subject, corresponding temporally correlated physiological reactions, a coupled emotional state and corresponding extracted profile characteristic features information about the respective other subjects obtained from profiles of the respective other subjects;
   employing a frequent pattern mining system to learn, from the historical data records, patterns that correlate the physiological reactions and answers to questions with profile characteristics features information obtained from the profiles of the respective other subjects;
   forming, in an off-line process, predictive model training datasets based on said historical data from said stored records and said learned patterns;
   running, using the hardware processor, a predictive model trained in the off-line process using said predictive model training datasets to recommend an action to administer augmented questions to said subject, said predictive model recommending the action based on the learned patterns that correlate the physiological reactions and answers from other subjects with profile characteristics features information about the respective other subjects obtained from profiles of the respective other subjects, said running the predictive model further comprising generating action templates for storage in a memory storage device in communication with said hardware processor, each action template relating the action to recommend based on a learned pattern correlating captured temporally-correlated physiological or emotional reaction in response to an augmented question-answer tuple and a profile characteristic feature;
   accessing, by the hardware processor, an action template to recommend a corresponding action;
   generating, using the hardware processor, a feedback signal for receipt by said remote interviewer over the communications network connection, said feedback signal indicating said recommended corresponding action; and
   administering to the subject, using the hardware processor, responsive to said received feedback signal, one or more augmented questions as a follow-up to the administered question based on the corresponding action recommendation from the action template.

2. The computer-implemented method of claim 1, further comprising:
   obtaining, using the hardware processor, a context of the question answered by the subject, wherein said generating one or more augmented questions to administer is further based on the subject's obtained context.

3. The computer-implemented method of claim 1, further comprising:
   generating, using the hardware processor, one or more annotated answers to said administered question based on the temporally correlated physiological features and emotion state; and
   recommending further actions, using said hardware processor, to be taken by an interviewer administering the questionnaire based on said annotated answers.

4. The computer-implemented method of claim 3, wherein said recommended actions comprises one or more selected from the group consisting of: asking a further question to clarify a given answer, asking for clarification regarding inconsistencies in answers, and asking a follow-up question to the provided answer.

5. The computer-implemented method of claim 4, further comprising:
   storing in the formed database, using the hardware processor, historical features profile data from each of a plurality of said other subjects;
   storing in the formed database, using the hardware processor, historical question features and corresponding answer features from questionnaires and answers from said each of the plurality of said other subjects;
   storing in the formed database, using the hardware processor, associated extracted characterizing features from the plurality of other subjects that match to question features and corresponding answer features from questionnaires administered to each of the plurality of said other subjects; and
   training, using the hardware processor, in the off-line process, the predictive model based on said stored historical features profile data, said stored historical question features and corresponding answer features from questionnaires, and said stored associated extracted characterizing features from the plurality of other subjects that match to question features and corresponding answer features from questionnaires administered to each of the plurality of said other subjects.

6. A computer-implemented system to augment or annotate answers to a questionnaire, the system comprising:
   a memory storage device, and
   a hardware processor, associated with said memory storage device, and configured to perform a method to:
      receive from a subject, via a computing system, an answer in response to a question administered to the subject by a remotely located interviewer over a communications network connection;
      use a sensor device for automatically capturing, contemporaneously with receiving the answer from the subject, a physiological reaction to the question, the sensor device integrated within a sensor network in communication with said computing system;
      temporally correlate physiological features associated with the physiological reaction with a time the answer is provided by the subject, said temporally correlating comprising invoking an operation to synchronize, using a system clock of the sensor network, said captured physiological reaction with an action event received;
      determine an emotional state of the subject based on the correlated physiological features;
      form question-answer data pairs from the received answers and administered questions;
      couple a data representing the subject's current emotional state to current question-answer data pairs to form respective augmented question-answer tuples;
      obtain question features and answer features from said formed augmented question answer tuples;
      extract one or more profile characteristic features of the subject from a profile information corresponding to the subject, said characteristic features determined by using a natural language parsing system to perform a textual and semantic matching with keywords associated with said question features and answer features;
      form, using the hardware processor, a database that collects, over time, historical data pertaining to a plurality of other subjects, said historical data comprising data records associating, for each respective other subject: past administered question features and corresponding received answer features associated with a question administered to the respective other subject, corresponding temporally correlated physiological reactions, a coupled emotional state and corresponding extracted profile characteristic features information about the respective other subjects obtained from profiles of the respective other subjects;
      employ a frequent pattern mining system to learn, from the historical data records, patterns that correlate the physiological reactions and answers to questions with profile characteristics features information obtained from the profiles of the respective other subjects;
      form in an off-line process predictive model training datasets based on said historical data from said data records and said learned patterns;
      run a predictive model trained in the off-line process using said predictive model training datasets to recommend an action to administer augmented questions to said subject, said predictive model recommending the action based on learned patterns that correlate the physiological reactions and answers from other subjects with profile characteristics features information about the respective other subjects obtained from profiles of the respective other subjects, said running of said predictive model further configuring said hardware processor to generate action templates for storage in the associated memory storage device, each action template relating the action to recommend based on a learned pattern correlating captured temporally-correlated physiological or emotional reaction in response to an augmented question-answer tuple and a profile characteristic feature;
      access an action template to recommend a corresponding action;
      generate a feedback signal for receipt by said remote interviewer over the communications network connection, said feedback signal indicating said recommended corresponding action; and
      administer to the subject, responsive to said received feedback signal, one or more augmented questions as a follow-up to the administered question based on the corresponding action recommendation from the action template.

7. The computer-implemented system of claim 6, wherein said hardware processor is further configured to:
   obtain a context of the question answered by the subject, wherein said generating one or more augmented questions to administer is further based on the subject's obtained context.

8. The computer-implemented system of claim 6, wherein said hardware processor is further configured to:
   generate one or more annotated answers to said administered question based on the correlated physiological features and emotion state; and
   recommend further actions to be taken by an interviewer administering the questionnaire based on said annotated answers.

9. The computer-implemented system of claim 8, wherein said recommended actions comprises one or more selected from the group consisting of: asking a further question to clarify a given answer, asking for clarification regarding inconsistencies in answers, and asking a follow-up question to the provided answer.

10. The computer-implemented system of claim 9, wherein said hardware processor is further configured to:
store in the formed database historical features profile data from each of a plurality of other subjects;
store in the formed database historical question features and corresponding answer features from questionnaires and answers from said each of the plurality of other subjects;
store in the formed database associated extracted characterizing features from the plurality of subjects that match to question features and corresponding answer features from questionnaires administered to each of the plurality of other subjects; and
train in the off-line process, the predictive model based on said stored historical features profile data, said stored historical question features and corresponding answer features from questionnaires, and said stored associated extracted characterizing features from the plurality of other subjects that match to question features and corresponding answer features from questionnaires administered to each of the plurality of other subjects.

11. A computer program product comprising a non-transitory computer-readable storage medium having a computer-readable program stored therein, wherein the computer-readable program, when executed on a computing device including at least one processor, causes the at least one processor to perform:
receiving from a subject, via a computing system, an answer in response to a question administered to the subject by a remotely located interviewer over a communications network connection;
using a sensor device for automatically capturing, contemporaneously with receiving said answer from the subject, a physiological reaction to the question, the sensor device integrated within a sensor network in communication with said computing system;
correlating physiological features associated with the physiological reaction with a time the answer is provided by the subject, said temporally correlating comprising invoking an operation to synchronize, using a system clock of the sensor network, said captured physiological reaction with an action event received;
determining an emotional state of the subject based on the correlated physiological features;
forming question-answer data pairs from the received answers and administered questions;
coupling a data representing the subject's current emotional state to current question-answer data pairs to form respective augmented question-answer tuples;
obtaining question features and answer features from said formed augmented question answer tuples;
extracting one or more profile characteristic features of the subject from a profile information corresponding to the subject, said characteristic features determined by using a natural language parsing system to perform a textual and semantic matching with keywords associated with said question features and answer features;
forming, using the hardware processor, a database that collects, over time, historical data pertaining to a plurality of other subjects, said historical data comprising data records associating, for each respective other subject: past administered question features and corresponding received answer features associated with a question administered to the respective other subject, corresponding temporally correlated physiological reactions, a coupled emotional state and corresponding extracted profile characteristic features information about the respective other subjects obtained from profiles of the respective other subjects;
employing a frequent pattern mining system to learn, from the historical data records, patterns that correlate the physiological reactions and answers to questions with profile characteristics features information obtained from the profiles of the respective other subjects;
forming in an off-line process predictive model training datasets based on said historical data from said stored records and said learned patterns;
running a predictive model trained in the off-line process using said predictive model training datasets to recommend an action to administer augmented questions to said subject, said predictive model recommending the action based on learned patterns that correlate the physiological reactions and answers from other subjects with profile characteristics features information about the respective subjects obtained from profiles of the respective other subjects, said running the predictive model further comprising generating action templates for storage in a memory storage device in communication with said at least one processor, each action template relating the action to recommend based on a learned pattern correlating captured temporally-correlated physiological or emotional reaction in response to an augmented question-answer tuple and a profile characteristic feature;
accessing an action template to recommend a corresponding action;
generating a feedback signal for receipt by said remote interviewer over the communications network connection, said feedback signal indicating said recommended corresponding action; and
administering to the subject, in response to said received feedback signal, one or more augmented questions as a follow-up to the administered question based on the corresponding action recommendation from the action template.

12. The computer program product of claim 11, wherein the computer-readable program, when executed on the computing device including the at least one processor, causes the at least one processor to perform:
obtaining a subject's emotion state based on the physiological reaction captured, wherein said generating one or more augmented questions to administer is further based on the subject's obtained emotion state.

13. The computer program product of claim 12, further comprising:
generating one or more annotated answers to said administered question based on the correlated physiological features and emotion state; and
recommending further actions to be taken by an interviewer administering the questionnaire based on said annotated answers.

14. The computer-implemented method of claim 1, wherein said extracting of one or more profile characteristic features further comprises:
passing unstructured data associated with the interviewee profile through an annotator to identify concepts of interest in the unstructured data.

15. The computer-implemented system of claim 6, wherein to extract one or more profile characteristic features, said hardware processor is further configured to:

pass unstructured data associated with the interviewee profile through an annotator to identify concepts of interest in the unstructured data.

16. The computer program product of claim 12, wherein the computer-readable program, when executed on the computing device including the at least one processor, causes the at least one processor to perform:

passing unstructured data associated with the interviewee profile through an annotator to identify concepts of interest in the unstructured data.

\* \* \* \* \*